United States Patent [19]
Cherpeck

[11] Patent Number: 5,427,591
[45] Date of Patent: Jun. 27, 1995

[54] POLY(OXYALKYLENE) HYDROXYAROMATIC ESTERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 993,179

[22] Filed: Dec. 18, 1992

[51] Int. Cl.$^6$ ............................................. C10L 1/18
[52] U.S. Cl. ............................... 44/400; 44/388; 560/61; 560/63
[58] Field of Search .............. 44/388, 387, 389, 400, 44/386, 385; 560/61, 63, 103

[56] References Cited

U.S. PATENT DOCUMENTS

| | | | |
|---|---|---|---|
| 2,800,400 | 7/1957 | Hughes | 44/389 |
| 2,937,933 | 5/1960 | Heisler et al. | 44/389 |
| 3,758,282 | 9/1973 | Owen et al. | 44/389 |
| 3,849,085 | 11/1974 | Kreuz et al. | 44/78 |
| 3,944,594 | 3/1976 | Kleiner et al. | 44/389 |
| 4,134,846 | 1/1979 | Machleder et al. | 252/51.5 |
| 4,191,537 | 3/1980 | Lewis et al. | 44/71 |
| 4,245,030 | 1/1981 | Faust et al. | 430/281 |
| 4,952,732 | 8/1990 | Speranza et al. | 564/390 |
| 5,211,721 | 5/1993 | Sung et al. | 44/400 |

*Primary Examiner*—Ellen M. McAvoy
*Attorney, Agent, or Firm*—C. J. Caroli

[57] ABSTRACT

Poly(oxyalkylene) hydroxyaromatic esters having the formula:

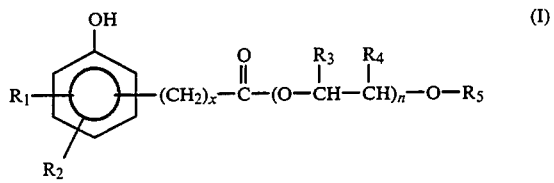

or a fuel-soluble salt thereof; where $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; $R_5$ is hydrogen, alkyl having 1 to 30 carbon atoms, phenyl, aralkyl or alkaryl having 7 to 36 carbon atoms, or an acyl group having the formula:

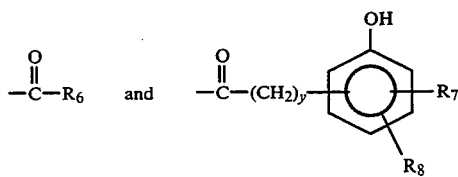

wherein $R_6$ is alkyl having 1 to 30 carbon atoms, phenyl, or aralkyl or alkaryl having 7 to 36 carbon atoms; $R_7$ and $R_8$ are each independently hydrogen, hydroxy, lower alkyl having 1 to 6 carbon atoms, or lower alkoxy having 1 to 6 carbon atoms; n is an integer from 5 to 100; and x and y are each independently an integer from 0 to 10.

The poly(oxyalkylene) hydroxyaromatic esters of formula I are useful as fuel additives for the prevention and control of engine deposits.

18 Claims, No Drawings

POLY(OXYALKYLENE) HYDROXYAROMATIC ESTERS AND FUEL COMPOSITIONS CONTAINING THE SAME

BACKGROUND OF THE INVENTION

1. Field of the Invention

This invention relates to novel hydroxyaromatic compounds. More particularly, this invention relates to novel poly (oxyalkylene) hydroxyaromatic esters and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amount of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, water repellent agents, paint adhesion promotors, and also as intermediates for preparing surfactants, and pololys finding use in the manufacture of polyurethane foam.

It has now been discovered that certain hydroxyaromatic esters having a poly(oxyalkylene) "tail" provide excellent control of engine deposits, especially intake valve deposits, when employed as fuel additives in fuel compositions. Moreover, these poly(oxyalkylene) hydroxyaromatic esters have been found to produce fewer combustion chamber deposits than known aliphatic hydrocarbon-substituted phenolic fuel additives.

SUMMARY OF THE INVENTION

The present invention provides novel poly(oxyalkylene) hydroxyaromatic esters which are useful as fuel additives for the prevention and control of engine deposits, particularly intake valve deposits.

The poly(oxyalkylene) hydroxyaromatic esters of the present invention have the formula:

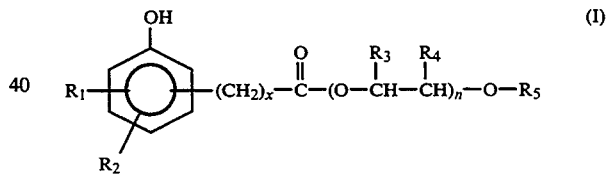

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; $R_5$ is hydrogen, alkyl having 1 to 30 carbon atoms, phenyl, aralkyl or alkaryl having 7 to 36 carbon atoms, or an acyl group of the formula:

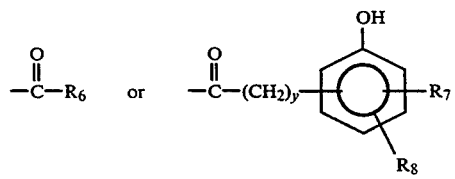

wherein $R_6$ is alkyl having 1 to 30 carbon atoms, phenyl, or aralkyl or alkaryl having 7 to 36 carbon atoms; $R_7$ and $R_8$ are each independently hydrogen, hydroxy, lower alkyl having 1 to 6 carbon atoms, or lower alkoxy having 1 to 6 carbon atoms; n is an integer from 5 to 100; and x and y are each independently an integer from 0 to 10.

The present invention further provides a fuel composition comprising a major amount of hydrocarbons boiling in the gasoline or diesel range and an effective deposit-controlling amount of a hydroxyaromatic poly(oxyalkylene) ester of the present invention.

The present invention additionally provides a fuel concentrate comprising an inert stable oleophilic organic solvent boiling in the range of from about 150° F. to 400° F. and from about 10 to 70 weight percent of a hydroxyaromatic poly(oxyalkylene) ester of the present invention.

Among other factors, the present invention is based on the surprising discovery that certain poly(oxyalkylene) hydroxyaromatic esters, when employed as fuel additives in fuel compositions, provide excellent control of engine deposits, especially on intake valves, and produce fewer combustion chamber deposits than known aliphatic hydrocarbon-substituted phenolic fuel additives.

DETAILED DESCRIPTION OF THE INVENTION

The fuel additives provided by the present invention have the general formula:

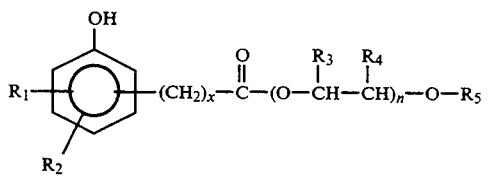

or a fuel-soluble salt thereof; wherein $R_1$, $R_2$, $R_3$, $R_4$, $R_5$, n and x are as defined hereinabove.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 2 to 22 carbon atoms, or alkylphenyl having an alkyl group containing 2 to 24 carbon atoms. More preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, $R_7$ is hydrogen, hydroxy, or lower alkyl having 1 to 4 carbon atoms. More preferably, $R_7$ is hydrogen or hydroxy. Most preferably, $R_7$ is hydrogen.

$R_8$ is preferably hydrogen.

Preferably, n is an integer from 10 to 50. More preferably, n is an integer from 15 to 30. Preferably, x is an integer from 0 to 2. More preferably, x is 0. Preferably, y is an integer from 0 to 2. More preferably, y is 0.

A preferred group of poly(oxyalkylene) hydroxyaromatic esters are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to about 22 carbon atoms or alkylphenyl having an alkyl group containing 4 to about 24 carbon atoms; n is 15 to 30 and x is 0.

Another preferred group of poly(oxyalkylene) hydroxyaromatic esters are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to about 22 carbon atoms or alkylphenyl having an alkyl group containing 4 to about 24 carbon atoms; n is 15 to 30 and x is 1 or 2.

A more preferred group of poly(oxyalkylene) hydroxyaromatic esters are those of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 4 to 12 carbon atoms or alkylphenyl having an alkyl group containing 4 to 12 carbon atoms; n is 15 to 30; and x is 0.

A particularly preferred group of poly(oxyalkylene) hydroxyaromatic esters are those having the formula:

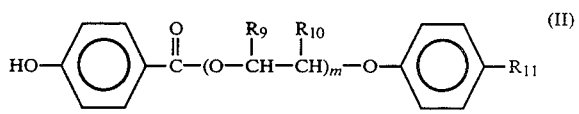

wherein one of $R_9$ and $R_{10}$ is methyl or ethyl and the other is hydrogen; $R_{11}$ is an alkyl group having 4 to 12 carbon atoms; and m is an integer from 15 to 30.

It is especially preferred that the aromatic hydroxyl group or groups present in the poly(oxyalkylene) hydroxyaromatic esters of this invention be situated in a meta or para position relative to the poly(oxyalkylene) ester moiety. When the aromatic moiety contains one hydroxyl group, it is particularly preferred that this hydroxyl group be in a para position relative to the poly(oxyalkylene) ester moiety.

The poly(oxyalkylene) hydroxyaromatic esters of the present invention will generally have a sufficient molecular weight so as to be non-volatile at normal engine intake valve operating temperatures (about 200°–250° C.). Typically, the molecular weight of the poly(oxyalkylene) hydroxyaromatic esters of this invention will range from about 600 to about 10,000, preferably from 1,000 to 3,000.

Generally, the poly(oxyalkylene) hydroxyaromatic esters of this invention will contain an average of about 5 to about 100 oxyalkylene units; preferably, 10 to 50 oxyalkylene units; more preferably, 15 to 30 oxyalkylene units.

Fuel-soluble salts of the poly(oxyalkylene) hydroxyaromatic esters of the present invention are also contemplated to be useful for preventing or controlling deposits. Such salts include alkali metal, alkaline earth metal, ammonium, substituted ammonium and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Definitions

As used herein the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_a$ wherein $R_a$ is lower alkyl. Typical lower alkoxy groups include methoxy, ethoxy, and the like.

The term "alkaryl" refers to the group:

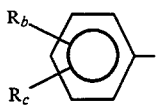

wherein $R_b$ and $R_c$ are each independently hydrogen or an alkyl group, with the proviso that both $R_b$ and $R_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_b$ is alkyl and $R_c$ is hydrogen.

The term "aralkyl" refers to the group:

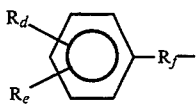

wherein $R_d$ and $R_e$ are each independently hydrogen or an alkyl group; and $R_f$ is an alkylene group. Typical alkaryl groups include, for example, benzyl, methylbenzyl, dimethylbenzyl, phenethyl, and the like.

The term "oxyalkylene unit" refers to an ether moiety having the general formula:

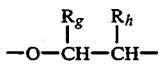

wherein $R_g$ and $R_h$ are each independently hydrogen or lower alkyl groups.

The term "poly(oxyalkylene)" refers to a polymer or oligomer having the general formula:

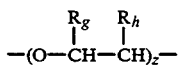

wherein $R_g$ and $R_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) hydroxyaromatic esters of this invention may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(oxyalkylene) hydroxyaromatic esters of the present invention having the formula:

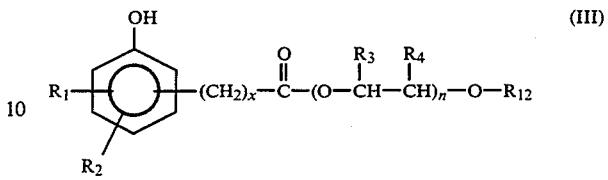

wherein $R_1$–$R_4$, n and x are as defined above and $R_{12}$ is an alkyl, phenyl, aralkyl or alkaryl group, may be prepared by esterifying a hydroxyaromatic carboxylic acid having the formula:

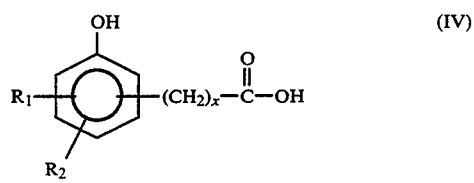

wherein $R_1$, $R_2$, and x are as defined above, with a poly(oxyalkylene) alcohol having the formula:

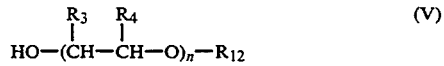

wherein $R_3$, $R_4$, $R_{12}$ and n are as defined above, using conventional esterification reaction conditions.

The hydroxyaromatic carboxylic acids of formula IV are either known compounds or can be prepared from known compounds by conventional procedures. Suitable hydroxyaromatic carboxylic acids for use as starting materials in this invention are 2-hydroxybenzoic acid, 3-hydroxybenzoic acid, 4-hydroxybenzoic acid, 3,4-dihydroxybenzoic acid, 3,4,5-trihydroxybenzoic acid, 3-hydroxy-4-methoxybenzoic acid, 4-hydroxy-3-methoxybenzoic acid, 3-t-butyl-4-hydroxybenzoic acid, 3,5-di-t-butyl-4-hydroxybenzoic acid, 4-hydroxyacetic acid, 3-(4-hydroxyphenyl)propionic acid and the like.

The poly(oxyalkylene) alcohols of formula V may also be prepared by conventional procedures known in the art. Such procedures are taught, for example, in U.S. Pat. Nos. 2,782,240 and 2,841,479, which are incorporated herein by reference.

Preferably, the poly(oxyalkylene) alcohols of formula V are prepared by contacting an alkoxide or phenoxide metal salt having the formula:

$$R_{12}OM \qquad (VI)$$

wherein $R_{12}$ is as defined above and M is a metal cation, such as lithium, sodium, or potassium, with about 5 to about 100 molar equivalents of an alkylene oxide (an epoxide) having the formula:

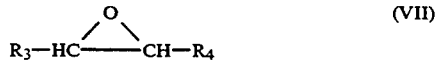

wherein $R_3$ and $R_4$ are as defined above.

Generally, metal salt VI is prepared by contacting the corresponding hydroxy compound $R_{12}OH$ with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt VI is generally not isolated, but is reacted in situ with the alkylene oxide VII to provide, after neutralization, the poly(oxyalkylene) alcohol V. This polymerization reaction is typically conducted in a substantially anhydrous inert solvent at a temperature of about $30°$ C. to about $150°$ C. for about 2 to about 120 hours. Suitable solvents for this reaction, include toluene, xylene and the like. The reaction will generally be conducted at a pressure sufficient to contain the reactants and the solvent, preferably at atmospheric or ambient pressure.

The amount of alkylene oxide employed in this reaction will depend on the number of oxyalkylene units desired in the product. Typically, the molar ratio of alkylene oxide VII to metal salt VI will range from about 5:1 to about 100:1; preferably, from 10:1 to 50:1; more preferably from 15:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g. propylene oxide, in which case the product is a homopolymer, e.g. a poly(oxypropylene). However, copolymers are equally satisfactory and random copolymers are readily prepared by contacting the metal salt with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt VI with first one alkylene oxide, then others in any order, or repetitively, under polymerization conditions.

The poly(oxyalkylene) alcohol V may also be prepared by living or immortal polymerization as described by S. Inoue and T. Aida in *Encyclopedia of Polymer Science and Engineering*, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

As noted above, the alkoxide or phenoxide metal salt VI is generally derived from the corresponding hydroxy compound, $R_{12}OH$. Preferred hydroxy compounds for use in this invention include straight- or branched-chain aliphatic alcohols having 1 to about 30 carbon atoms and phenols having the formula:

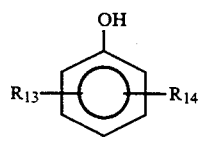

(VIII)

wherein $R_{13}$ and $R_{14}$ are each independently hydrogen or an alkyl group having 1 to about 30 carbon atoms. Preferably, the straight- or branched-chain aliphatic alcohols employed in this invention will contain 2 to about 22 carbon atoms, more preferably 4 to 12 carbon atoms. Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 30 carbon atoms. Particularly preferred aliphatic alcohols are butanols.

The alkylphenols of formula VIII used in this invention may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenols employed in this invention will contain 4 to about 24 carbon atoms, more preferably 4 to 12 carbon atoms. Representative examples of phenols suitable for use in this invention include, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are those derived from alkylation of phenol with polymers or oligomers of $C_3$ to $C_6$ olefins, such as polypropylene or polybutene. These polymers preferably contain 10 to 30 carbon atoms. An especially preferred alkylphenol is prepared by alkylating phenol with a propylene polymer having an average of 4 units. This polymer has the common name of propylene tetramer and is commercially available.

As indicated above, the poly(oxyalkylene) hydroxyaromatic esters of formula III may be prepared by esterifying a hydroxyaromatic carboxylic acid of formula IV with a poly(oxyalkylene) alcohol of formula V under conventional esterification reaction conditions.

Typically, this reaction will be conducted by contacting a poly(oxyalkylene) alcohol of formula V with about 0.25 to about 1.5 molar equivalents of a hydroxyaromatic carboxylic acid of formula IV in the presence of acidic catalyst at a temperature in the range of $70°$ C. to about $160°$ C. for about 0.5 to about 48 hours. Suitable acid catalysts for this reaction include p-toluenesulfonic acid, methanesulfonic acid and the like. The reaction may be conducted in the presence or absence of an inert solvent, such as benzene, toluene and the like. The water generated by this reaction is preferably removed during the course of the reaction by, for example, azeotropic distillation with an inert solvent, such as toluene.

The poly(oxyalkylene) hydroxyaromatic esters of formula III may also be synthesized by reacting a poly(oxyalkylene) alcohol of formula V with an acyl halide having the formula:

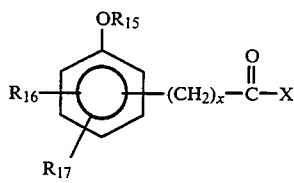 (IX)

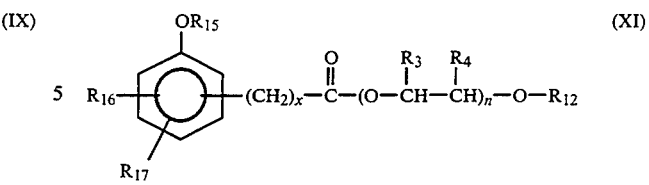 (XI)

wherein X is a halide, such as chloride or bromide, and $R_{15}$ is a suitable hydroxyl protecting group, such as benzyl, tert-butyldimethylsilyl, methoxymethyl, and the like; $R_{16}$ and $R_{17}$ are each independently hydrogen, lower alkyl, lower alkoxy, or the group $-OR_{18}$, wherein $R_{18}$ is a suitable hydroxyl protecting group.

Acyl halides of formula IX may be prepared from hydroxyaromatic carboxylic acids of formula IV by first protecting the aromatic hydroxyl groups of IV to form a carboxylic acid having the formula:

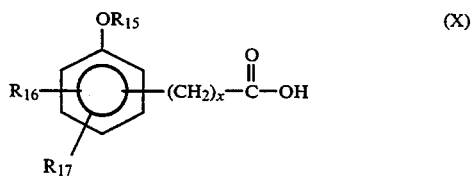 (X)

wherein $R_{15}$-$R_{17}$ and x are as defined above, and then converting the carboxylic acid moiety of X into an acyl halide using conventional procedures.

Protection of the aromatic hydroxyl groups of IV may be accomplished using well known procedures. The choice of a suitable protecting group for a particular hydroxyaromatic carboxylic acid will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein. Alternatively, the protected derivatives X can be prepared from known starting materials other than the hydroxyaromatic compounds of formula IV by conventional procedures.

The carboxylic acid moiety of X may be converted into an acyl halide by contacting X with an inorganic acid halide, such as thionyl chloride, phosphorous trichloride, phosphorous tribromide, or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

In certain cases where the hydroxyaromatic carboxylic acids of formula IV having bulky alkyl groups adjacent to the hydroxyl group, such as 3,5-di-t-butyl-4-hydroxybenzoic acid, it will generally not be necessary to protect the hydroxyl group prior to formation of the acyl halide, since such hydroxyl groups are sufficiently sterically hindered so as to be substantially non-reactive with the acyl halide moiety.

Reaction of acyl halide IX with poly(oxyalkylene) alcohol V provides an intermediate poly(oxyalkylene) ester having the formula:

wherein $R_3$, $R_4$, $R_{12}$, $R_{15}$-$R_{17}$, n and x are as defined above.

Typically, this reaction is conducted by contacting V with about 0.9 to about 1.5 molar equivalents of IX in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine or 4-dimethylaminopyridine.

Deprotection of the aromatic hydroxyl group(s) of XI then provides a poly(oxyalkylene) hydroxyaromatic ester of formula III. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

The poly(oxyalkylene) hydroxyaromatic esters of the present invention having the formula:

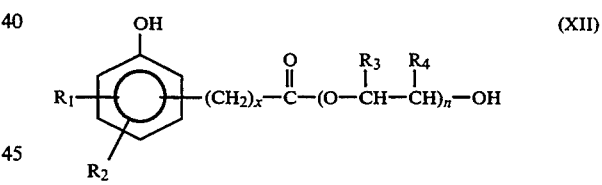 (XII)

wherein $R_1$-$R_4$, n and x are as defined above, can be prepared from compounds of formula III or XI, wherein $R_{12}$ is a benzyl group, by removing the benzyl group using conventional hydrogenolysis procedures. Compounds of formula III or XI where $R_{12}$ represents a benzyl group may be prepared by employing a metal salt VI derived from benzyl alcohol in the above described synthetic procedures.

Similarly, the poly(oxyalkylene) hydroxyaromatic esters of the present invention having the formula:

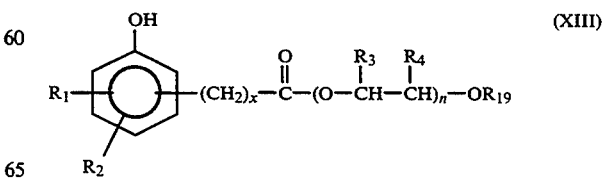 (XIII)

wherein $R_1$-$R_4$, n and x are as defined above and $R_9$ is an acyl group having the formula:

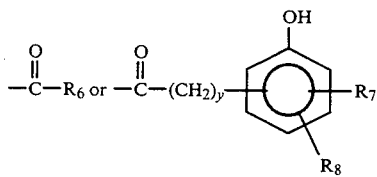

wherein $R_6$–$R_8$ and y are as defined above, can be synthesized in several steps from a compound of formula XI, wherein $R_{12}$ represents a benzyl group and $R_{15}$ (and optionally $R_{18}$) represents a hydroxyl protecting group that is stable to hydrogenolysis conditions, such as a tert-butyldimethylsilyl group. The synthesis of XIII from such compounds may be effected by first removing the benzyl group using conventional hydrogenolysis conditions and then acylating the resulting hydroxyl group with a suitable acylating agent. Removal of the protecting group(s) from the aromatic hydroxyl group(s) using conventional procedures then provides a poly(oxyalkylene) hydroxyaromatic ester of formula XIII.

Suitable acylating agents for use in this reaction include acyl halides, such as acyl chlorides and bromides; and carboxylic acid anhydrides. Preferred acylating agents are those having the formula: $R_6C(O)$—X, wherein $R_6$ is alkyl having 1 to 30 carbon atom, phenyl, or aralkyl or alkaryl having 7 to 36 carbon atoms, and X is chloro or bromo; and those having the formula:

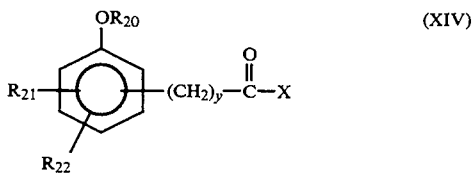

wherein X is a halide, such as chloride or bromide, $R_{20}$ is a suitable hydroxyl protecting group, $R_{21}$ and $R_{22}$ are each independently hydrogen, lower alkyl, lower alkoxy, or the group —$OR_{23}$, wherein $R_{23}$ is a suitable hydroxyl protecting group, and y is an integer from 0 to 10.

A particularly preferred group of acylating agents are those having the formula: $R_{24}C(O)$—X, wherein $R_{24}$ is alkyl having 4 to 12 carbon atoms. Representative examples of such acylating agents include acetyl chloride, propionyl chloride, butanoyl chloride, pivaloyl chloride, octanoyl chloride, decanoyl chloride and the like.

Another particularly preferred group of acylating agents are those of formula XIV, wherein $R_{20}$ is benzyl; $R_{21}$ is hydrogen, alkyl having 1 to 4 carbon atoms, or —$OR_{25}$, wherein $R_{25}$ is a suitable hydroxyl protecting group, preferably benzyl; $R_{22}$ is hydrogen; and y is 0, 1 or 2. Representative examples of such acylating agents include 4-benzyloxybenzoyl chloride, 3-benzyloxybenzoyl chloride, 4-benzyloxy-3-methylbenzoyl chloride, 4-benzyloxyphenylacetyl chloride, 3-(4-benzyloxyphenyl)propionyl chloride and the like.

Generally, this acylation reaction will be conducted using about 0.95 to about 1.2 molar equivalents of the acylating agent. The reaction is typically conducted in an inert solvent, such as toluene, dichloromethane, diethyl ether and the like, at a temperature in the range of about 25° C. to about 150° C. for about 0.5 to about 48 hours. When an acyl halide is employed as the acylating agent, the reaction is preferably conducted in the presence of a sufficient amount of an amine capable of neutralizing the acid generated during the reaction, such as triethylamine, di(isopropyl)-ethylamine, pyridine or 4-dimethylaminopyridine.

A particularly preferred group of poly(oxyalkylene) hydroxyaromatic esters of formula XIII are those having the same hydroxyaromatic ester group at each end the poly(oxyalkylene) moiety, i.e. compounds of formula XIII wherein $R_{19}$ is an acyl group having the formula:

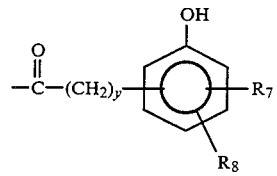

wherein $R_7$ is the same group as $R_1$, $R_8$ is the same group as $R_2$, and x and y are the same integer.

These compounds may be prepared from a poly(oxyalkylene) diol having the formula:

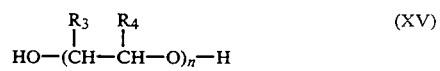

wherein $R_3$, $R_4$, and n are as defined above, by esterifying each of the hydroxyl groups present in XV with a hydroxyaromatic carboxylic acid of formula IV or an acyl halide of formula IX using the above described synthetic procedures. The poly(oxyalkylene) diols of formula XV are commercially available or may be prepared by conventional procedures, for example, by using sodium or potassium hydroxide in place of the alkoxide or phenoxide metal salt VI in the above described alkylene oxide polymerization reaction.

Fuel Compositions

The poly(oxyalkylene) hydroxyaromatic esters of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the poly(oxyalkylene) hydroxyaromatic esters of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) hydroxyaromatic esters of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) hydroxyaromatic esters of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis.

These carrier fluids are believed to act as a carrier for the fuel additives of the present invention and to assist in removing and retarding deposits. The carrier fluid may also exhibit synergistic deposit control properties when used in combination with a hydroxyaromatic poly(oxyalkylene) compound of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and should not be interpreted as limitations upon the scope of the invention.

Example 1

Preparation of 4-Benzyloxybenzoyl Chloride

To a flask equipped with a magnetic stirrer and drying tube was added 10.0 grams of 4-benzyloxybenzoic acid and 100 mL of anhydrous diethyl ether and then 19.1 mL of oxalyl chloride. The resulting mixture was stirred at room temperature for 16 hours and then the solvent was removed in vacuo to yield 10.8 grams of the desired acid chloride.

Example 2

Preparation of α(4-Benzyloxybenzoyl)-ω-4-dodecylphenoxypoly(oxybutylene)

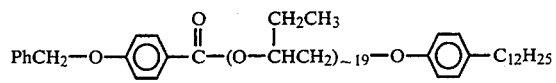

4-Benzyloxybenzoyl chloride (10.8 grams) from Example 1 was combined with 72.2 grams of α-hydroxy-ω-4-dodecylphenoxypoly(oxybutylene) having an average of 19 oxybutylene units (prepared essentially as described in Example 6 of U.S. Pat. No. 4,160,648) and 150 mL of anhydrous toluene. Triethylamine (6.41 mL) and 4-dimethylaminopyridine (0.54 grams) were then added and the resulting mixture was heated to reflux under nitrogen for 16 hours. The reaction was then cooled to room temperature and diluted with 300 mL of diethyl ether. The organic layer was washed twice with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 76.5 grams of a light brown oil. The oil was chromatographed on silica gel, eluting with hexane/diethyl ether/ethanol (8:1.5:0.5), to yield 43.2 grams of the desired product as a colorless oil.

Example 3

Preparation of α-(4-Hydroxybenzoyl) -ω-4-dodecylphenoxypoly(oxybutylene)

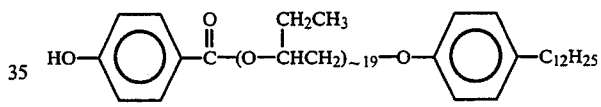

A solution of 15.9 grams of the product from Example 2 in 50 mL of ethyl acetate and 50 mL of acetic acid containing 3.48 grams of 5% palladium on charcoal was hydrogenolyzed at 35–40 psi for 16 hours on a Parr low-pressure hydrogenator. Catalyst filtration and removal of residual acetic acid with toluene in vacuo yielded 14.6 grams of the desired product as a colorless oil. The product had an average of 19 oxybutylene units. IR (neat) 1715 cm$^{-1}$; $^1$H NMR (CDCl$_3$) δ 7.9, 7.3 (AB quartet, 4H), 7.1–7.25 (m, 2H), 6.7–6.9 (m, 2H), 5.05–5.15 (m, 1H), 3.1–4.0 (m, 56H), 0.5–1.9 (m, 120H).

Similarly, by using the above procedures and the appropriate starting materials and reagents, the following compounds can by prepared:

α-(4-hydroxybenzoyl)-ω-n-butyloxypoly (oxybutylene);

α-(4-hydroxybenzoyl)-ω-4 -t-butylphenoxypoly(oxybutylene);

α-(4-hydroxybenzoyl)-ω-4-octacosylphenoxypoly(oxybutylene);

α-(4-hydroxy-3-methoxybenzoyl)-ω-4-dodecylphenoxypoly(oxybutylene);

α-(4-hydroxy-3-methybenzoyl)-ω-4-dodecylphenoxypoly(oxybutylene); and

α-(3,4-dihydroxybenzoyl)-ω-4-dodecylphenoxypoly(oxybutylene).

Example 4

Preparation of α-(4-Hydroxybenzoyl)-ω-n-butoxypoly(oxypropylene)

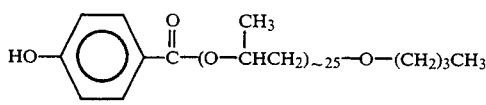

To a flask equipped with a magnetic stirrer, thermometer, Dean-Stark trap, nitrogen inlet and reflux condenser was added 4.52 grams of 4-hydroxybenzoic acid, 50.0 grams of α-hydroxy-ω-n-butoxypoly(oxypropylene) having an average of 25 oxypropylene units (commercially available from Union Carbide as LB385) and 0.56 grams of p-toluenesulfonic acid. The reaction was heated to 120° C. for 16 hours and then cooled to room temperature. Diethyl ether (750 mL) was added and the organic phase was washed twice with saturated aqueous sodium bicarbonate, and once with saturate aqueous sodium chloride solution. The organic layer was then dried over anhydrous magnesium sulfate, filtered and concentrated in vacuo to afford 51.7 grams of a brown oil. The oil was chromatographed on silica gel, eluting with hexane/ethyl acetate/ethanol (49:49:2) to yield 25.2 grams of the desired product as a yellow oil. The product had an average of 25 oxypropylene units. IR (neat) 1715 cm$^{-1}$; $^1$H NMR (CDCl$_3$) δ 7.9, 6.85 (AB quartet, 4H), 5.05–5.15 (m, 1H), 3.1–4.0 (m, 76H), 1.4–1.6 (m, 2H), 1.25–1.4 (m, 2H), 0.9–1.4 (m, 75H), 75–0.9 (t, 3H).

Similarly, by using the above procedures and the appropriate starting materials and reagents, the following compounds can by prepared:

α-(4-hydroxybenzoyl)-ω-4-t-butylphenoxypoly(oxypropylene);

α-(4-hydroxybenzoyl )-ω-4-dodecylphenoxypoly(oxypropylene);

α-(4-hydroxy-3-methoxybenzoyl)-ω-n-butoxypoly(oxypropylene);

α-(4-hydroxy-3-methybenzoyl)-ω-n-butoxypoly (oxypropylene); and

α-(3,4 -dihydroxybenzoyl)-ω-n-butoxypoly(oxybutylene) .

Example 5

Preparation of 2-Benzyloxybenzoyl Chloride

To a flask equipped with a magnetic stirrer and drying tube was added 15.0 grams of 2-benzyloxybenzoic acid and 150 mL of anhydrous dichloromethane followed by 28.7 mL of oxalyl chloride. The reaction was stirred at room temperature for 16 hours, and then the solvent was removed in vacuo to yield 16.2 grams of the desired acid chloride.

Example 6

Preparation of α-(2-Benzyloxybenzoyl)-ω-4-dodecylphenoxypoly(oxybutylene)

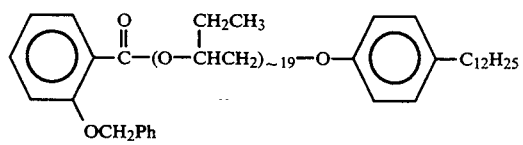

2-Benzyloxybenzoyl chloride (16.2 grams) from Example 5 was combined with 108.3 grams of α-hydroxy-ω-4-dodecylphenoxypoly(oxybutylene) having an average of 19 oxybutylene units (prepared essentially as described in Example 6 of U.S. Pat. No. 4,160,648) and 225 mL of anhydrous toluene. Triethylamine (9.6 mL) and 4-dimethylaminopyridine (0.8 grams) were added and the reaction was heated to reflux under nitrogen for 16 hours, then cooled to room temperature and diluted with 500 mL of diethyl ether. The organic layer was washed twice with 1% aqueous hydrochloric acid, twice with saturated aqueous sodium bicarbonate solution, and once with saturated aqueous sodium chloride. The organic layer was then dried over anhydrous magnesium sulfate, filtered and concentrated in vacuo to yield 119.2 grams of a light brown oil. The oil was chromatographed on silica gel, eluting with hexane/diethyl ether/ethanol (8:1.5:0.5) to yield 73.0 grams of the desired product as a light brown oil.

Example 7

Preparation of α(2-Hydroxybenzoyl)-ω-4-dodecylphenoxypoly(oxybutylene)

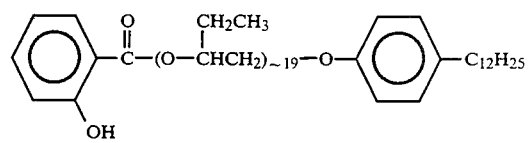

A solution of 30.8 grams of the product from Example 6 in 95 mL of ethyl acetate and 95 mL of acetic acid containing 3.39 grams of 10% palladium on charcoal was hydrogenolyzed at 35–40 psi for 16 hours on a Parr low-pressure hydrogenator. Catalyst filtration and removal of solvent in vacuo followed by azeotropic removal of residual acetic acid with toluene under vacuum yielded 28.9 grams of the desired product as a light brown oil. The product had an average of 19 oxybutylene units. IR (neat) 1673 cm$^{-1}$, $^1$H NMR (CDCL3) δ 10.85 (s, 1H), 7.8–8.2 (m, 8H), 5.1–5.3 (m, 1H), 3.2–4.1 (m, 56H), 0.5–1.9 (m, 21H).

Example 8

Preparation of α(3-Hydroxybenzoyl)-ω-4-dodecylphenoxypoly(oxybutylene)

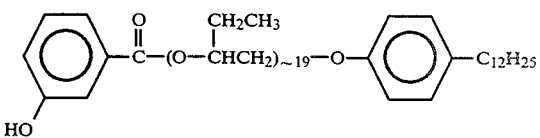

To a flask equipped with a magnetic stirrer, thermometer, Dean-Stark trap, nitrogen inlet and reflux condenser was added 5.08 grams of 3-hydroxybenzoic acid, 50.0 grams of α-hydroxy-ω-4-dodecylphenoxypoly(oxybutylene) having an average of 19 oxybutylene units (prepared essentially as described in Example 6 of U.S. Pat. No. 4,160,648) and 0.53 grams of p-toluenesulfonic acid. The reaction was heated to 130° C. for 48 hours and then cooled to room temperature. Diethyl ether (750 mL) was added and the organic phase was washed twice with saturated aqueous sodium bicarbonate and once with saturated aqueous sodium chloride solution. The organic layer was then dried over anhydrous magnesium sulfate, filtered and concentrated in vacuo to afford 47.8 grams of a brown oil. The oil was chromatographed on silica gel, eluting with hexane/ethyl acetate/ethanol (78:20:2) to yield 16.5 grams of the desired product as a yellow oil. The product had an average of 19 oxybutylene groups. IR (neat) 1716 cm$^{-1}$; $^1$H NMR (CDCl$_3$) δ 6.6–7.6 (m, 8H), 4.9–5.2 (m, 1H), 3.1–4.0 (m, 56H), 0.5–1.9 (m, 21H).

Example 9

Preparation of 3,5-Di-t-butyl-4-hydroxybenzoyl Chloride

To a flask equipped with a magnetic stirrer, reflux condenser and nitrogen inlet was added 1.88 grams of 3,5-di-t-butyl-4-hydroxybenzoic acid and 15 mL of thionyl chloride. The reaction was refluxed for 2 hours and stirred at room temperature for 16 hours. The excess thionyl chloride was removed in vacuo to yield 2.2 grams of the desired acid chloride as a white solid.

Example 10

Preparation of α-(3,5-Di-t-butyl-4-hydroxybenzoyl)-ω-4-dodecylphenoxypoly(oxybutylene)

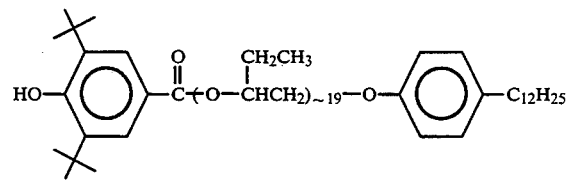

3,5-Di-t-butyl-4-hydroxybenzoyl chloride (2.2 grams) from Example 9 was combined with 13.6 grams of α-hydroxy-ω-4-dodecylphenoxy-poly(oxybutylene) having an average of 19 oxybutylene units (prepared essentially as described in Example 6 of U.S. Pat. No. 4,160,648) and 50 mL of anhydrous toluene. Triethylamine (1.17 mL) and 4-dimethylaminopyridine (0.1 grams) were added and the reaction was heated to reflux under nitrogen for 16 hours, and then cooled to room temperature and diluted with 100 mL of hexane. The organic layer was washed twice with water, once with saturated aqueous sodium bicarbonate solution and once with saturated aqueous sodium chloride. The organic layer was dried over anhydrous magnesium sulfate, filtered and concentrated in vacuo to give an oil. The oil was chromatographed on silica gel, eluting with hexane/diethyl ether/ethanol (6:3.5:0.5) to yield 3.0 grams of the desired product as a yellow oil. IR (neat) 1715 cm$^{-1}$; $^1$H NMR (CDCl$_3$) δ 7.8 (s, 2H), 7.1–7.25 (m, 2H), 6.7–6.9 (m, 2H), 5.7 (s, 1H), 7.1–7.25 (m, 2H), 6.7–6.9 (m, 2H), 5.7 (s, 1H), 5.05–5.15 (m, 1H), 3.1–4.0 (m, 56H), 0.5–1.9 (m, 138H).

Example 11

Preparation of α-(3,5-Di-t-butyl-4-hydroxybenzoyl)-ω-n-butoxypoly(oxypropylene)

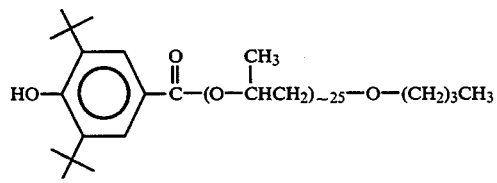

3,5-Di-t-butyl-4-hydroxybenzoyl chloride (8.0 grams) prepared as described in Example 9 was combined with 46.2 grams of α-hydroxy-ω-n-butoxypoly(oxypropylene) having an average of 25 oxypropylene units (commercially available from Union Carbide as LB385) and 200 mL of anhydrous toluene. Triethylamine (4.4 mL) and 4-dimethylaminopyridine (0.37 grams) were added and the reaction was heated to reflux under nitrogen for 16 hours, and then cooled to room temperature and diluted with 500 mL of hexane. The organic layer was washed twice with water, once with saturated aqueous sodium bicarbonate solution and once with saturated aqueous sodium chloride. The organic layer was dried over anhydrous magnesium sulfate, filtered and concentrated in vacuo to give an oil. The oil was chromatographed on silica gel, eluting with hexane/diethyl ether/ethanol (6:3.5:0.5) to yield 42.0 grams of the desired product as a yellow oil. The product had an average of 25 oxypropylene units. IR (neat) 1715 cm$^{-1}$; $^1$H NMR (CDCl$_3$) δ 7.8 (s, 2H), 5.7 (s, 1H), 5.05–5.15 (m, 1H), 3.2–3.9 (m, 75H), 0.9–1.6 (m, 97H), 0,75–0.9 (t, 3H).

Example 12

Preparation of α-[(4-Hydroxyphenyl)acetyl]-ω-4-dodecylphenoxypoly(oxybutylene)

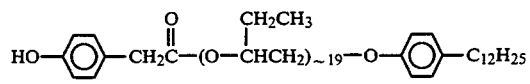

To a flask equipped with a magnetic stirrer, thermometer, Dean-Stark trap, nitrogen inlet and reflux condenser was added 4.66 grams of 4-hydroxyphenylacetic acid, 50.0 grams of α-hydroxy-ω-4-dodecylphenoxypoly(oxybutylene) having an average of 19 oxybutylene units (prepared essentially as described in Example 6 of U.S. Pat. No. 4,160,648) and 0.63 grams of p-toluenesulfonic acid. The reaction was heated to 120° C. for 16 hours and then cooled to room temperature. Diethyl ether (750 mL) was added and the organic phase was washed twice with saturated aqueous sodium bicarbonate, and then once with saturated aqueous sodium chloride solution. The organic layer was dried over anhydrous magnesium sulfate, filtered and concentrated in vacuo to afford 51.6 grams of a brown oil. The oil was chromatographed on silica gel, eluting with hexane/ethyl acetate/ethanol (93:5:2) to yield 26.2 grams of the desired product as a yellow oil. The product had an average of 19 oxybutylene units. IR (neat) 1742 cm$^{-1}$; $^1$H NMR (CDCl$_3$) δ 6.7–7.25 (m, 8H), 4.8–5.0 (m, 1H), 3.1–4.05 (m, 58H), 0.5–1.9 (m, 120H).

Example 13

Preparation of α- [3-(4-Hydroxyphenyl)propionyl]-ω-4-dodecylphenoxypoly(oxybutylene)

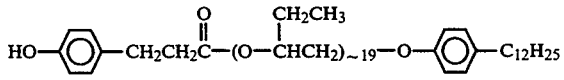

To a flask equipped with a magnetic stirrer, thermometer, Dean-Stark trap, nitrogen inlet and reflux condenser was added 5.09 grams of 3-(4-hydroxyphenyl)propionic acid, 50.0 grams of α-hydroxy-ω-4-dodecylphenoxypoly(oxybutylene) having an average of 19 oxybutylene units (prepared essentially as described in Example 6 of U.S. Pat. No. 4,160,648) and 0.63 grams of p-toluenesulfonic acid. The reaction was heated to 120° C. for 16 hours and then cooled to room temperature. Diethyl ether (750 mL) was added and the organic phase was washed twice with saturated aqueous sodium bicarbonate, and once with saturated aqueous sodium chloride solution. The organic layer was dried over anhydrous magnesium sulfate, filtered and concentrated in vacuo to afford 52.7 grams of a brown oil. The oil was chromatographed on silica gel, eluting with hexane/ethyl acetate/ethanol (93:5:2) to yield 37.5 grams of the desired product as a yellow oil. IR (neat) 1735 cm$^{-1}$; $^1$H NMR (CDCl$_3$) δ 6.7–7.25 (m, 8H), 4.8–5.0 (m, 1H), 3.1–4.05 (m, 56H), 2.9 (t, 2H), 2.55 (t, 2H), 0.5–0.9 (m, 120H).

Example 14

Preparation of α-Benzyloxy-ω-4-hydroxypoly(oxybutylene)

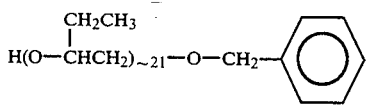

To a flask equipped with a mechanical stirrer, thermometer, addition funnel, reflux condenser and nitrogen inlet was added 1.59 grams of a 35 wt.% dispersion of potassium hydride in mineral oil. Benzyl alcohol (5.0 grams) dissolved in 250 mL of anhydrous toluene was added dropwise. After hydrogen evolution had subsided, the reaction was heated to reflux for 3 hours and then cooled to room temperature. 1,2-Epoxybutane (99.6 mL) were then added dropwise and the reaction was refluxed for 16 hours. The reaction was cooled to room temperature, quenched with 5 mL of methanol and diluted with 500 mL of diethyl ether. The resulting mixture was washed with saturated aqueous ammonium chloride, followed by water and saturated aqueous sodium chloride. The organic layer was dried over anhydrous magnesium sulfate, filtered and the solvents removed in vacuo to yield 64.1 grams of a yellow oil, The oil was chromatographed on silica gel, eluting with hexane/ethyl acetate/ethanol (90:8:2) to afford 40 grams of the desired product as a light yellow oil.

Example 15

Preparation of α-(4-Benzyloxybenzoyl)-ω-benzyloxypoly(oxybutylene)

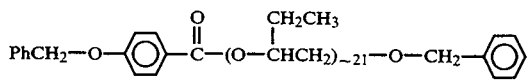

4-Benzyloxybenzoyl chloride (10.8 grams) from Example 1 was combined with α-benzyloxy-ω-hydroxypoly(oxybutylene) (15.0 grams) from Example 14 and 50 mL of anhydrous toluene. Triethylamine (1.3 mL) and 4-dimethylaminopyridine (0.55 grams) were then added and the resulting mixture was heated to reflux under nitrogen for 16 hours. The reaction was then cooled to room temperature and diluted with 100 mL of diethyl ether. The organic layer was washed twice with 1% aqueous hydrochloric acid, twice with saturated aqueous sodium bicarbonate solution, and once with saturated aqueous sodium chloride. The organic layer was then dried over anhydrous magnesium sulfate, filtered and the solvents removed in vacuo to yield 16.8 grams of the desired product as a yellow oil.

Example 16

Preparation of α-(4-Hydroxybenzoyl)-ω-hydroxypoly(oxybutylene)

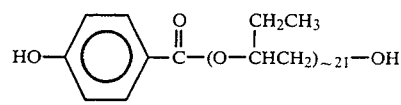

A solution of 16.8 grams of the product from Example 15 in 100 mL of ethyl acetate and 100 mL of acetic acid containing 3.0 grams of 5% palladium on charcoal was hydrogenolyzed at 35–40 psi for 16 hours on a Parr low-pressure hydrogenator. Catalyst filtration and removal of residual acetic acid with toluene in vacuo yielded 14.8 grams of the desired product as a yellow oil. The product had an average of 21 oxybutylene units. IR (neat) 1715 cm$^{-1}$; $^1$H NMR (CDCl$_3$) δ 7.9, 6.8 (AB quartet, 4H), 5.05–5.15 (m, 1H), 3.1–3.9 (m, 62H), 0.6–1.9 (m, 105H).

Comparative Example A

Preparation of Polyisobutylphenol

To a flask equipped with a magnetic stirrer, reflux condenser, thermometer, addition funnel and nitrogen inlet was added 203.2 grams of phenol. The phenol was warmed to 40° C. and boron trifluoride etherate (73.5 mL) was added dropwise. Ultravis 10 polyisobutene (1040 grams, molecular weight 950, 76% methylvinylidene isomer, available from British Petroleum), dissolved in 1,863 mL of hexane, was then added to the reaction mixture at a rate sufficient to maintain the temperature between 22°–27° C. The reaction mixture was then stirred for 16 hours at room temperature. Concentrated ammonium hydroxide (400 mL) was then added and the mixture was diluted with 2 L of hexane. The resulting mixture was washed with water (3×2 L), dried over anhydrous magnesium sulfate, filtered and the solvent removed in vacuo to yield 1,056.5 grams of an oil. This oil was determined to contain 80% of the desired polyisobutenylphenol and 20% polyisobutene by $^1$H NMR and also by chromatography on silica gel, eluting first with hexane and then with hexane/ethyl acetate/ethanol (93:5:2).

Example 17

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 214.7 | 193.7 | 204.2 |
| Example 3 | 7.1 | 9.1 | 8.1 |
| Example 4 | 127.7 | 128.4 | 128.1 |
| Example 7 | 150.0 | 215.4 | 182.7 |
| Example 8 | 62.3 | 57.5 | 59.9 |
| Example 10 | 108.0 | 95.1 | 101.6 |
| Example 11 | 117.1 | 124.6 | 120.9 |
| Example 12 | 84.6 | 98.4 | 91.5 |
| Example 13 | 90.5 | 90.7 | 90.6 |
| Example 16 | 41.1 | 43.0 | 42.1 |

[1] At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the poly(oxyalkylene) hydroxyaromatic esters of the present invention (Examples 3, 4, 7, 8, 10, 11, 12, 16) compared to the base fuel.

Example 18

Multicylinder Engine Test

The poly(oxyalkylene) hydroxyaromatic esters of the present invention were tested in a laboratory multicylinder engine to evaluate their intake valve and combustion chamber deposit control performance. The test engine was a 4.3 liter, TBI (throttle body injected), V6 engine manufactured by General Motors Corporation. The major engine dimensions are set forth in Table II:

TABLE II

| Engine Dimensions | |
|---|---|
| Bore | 10.16 cm |
| Stroke | 8.84 cm |
| Displacement Volume | 4.3 liter |
| Compression Ratio | 9.3:1 |

The test engine was operated for 40 hours (24 hours a day) on a prescribed load and speed schedule representative of typical driving conditions. The cycle for engine operation during the test is set forth in Table III.

TABLE III

| | | Engine Driving Cycle | | |
|---|---|---|---|---|
| Step | Mode | Time in Mode [Sec][1] | Dynamometer Load [kg] | Engine Speed [RPM] |
| 1 | Idle | 60 | 0 | 800 |
| 2 | City Cruise | 150 | 10 | 1,500 |
| 3 | Acceleration | 40 | 25 | 2,800 |
| 4 | Heavy HWY Cruise | 210 | 15 | 2,200 |
| 5 | Light HWY Cruise | 60 | 10 | 2,200 |
| 6 | Idle | 60 | 0 | 800 |
| 7 | City Cruise | 180 | 10 | 1,500 |
| 8 | Idle | 60 | 0 | 800 |

[1] All steps, except step number 3, include a 15 second transition ramp. Step 3 includes a 20 second transition ramp.

All of the test runs were made with the same base gasoline, which was representative of commercial unleaded fuel. The results are set forth in Table IV.

TABLE IV

| Sample[1] | Multicylinder Engine Test Results | | |
|---|---|---|---|
| | | Intake Valve Deposits[2] | Combustion Chamber Deposits[2] |
| Base Fuel | Run 1 | 951 | 1887 |
| | Run 2 | 993 | 1916 |
| | Average | 972 | 1902 |
| Example 3 | Run 1 | 48 | 2173 |
| | Run 2 | 48 | 2205 |
| | Average | 48 | 2189 |
| Comparative Example A | Run 1 | 229 | 2699 |
| | Run 2 | 218 | 2738 |
| | Average | 224 | 2719 |

[1] At 400 parts per million actives (ppma).
[2] In milligrams (mg).

The base fuel employed in the above multicylinder engine tests contained no fuel detergent. The test compounds were admixed with the base fuel to give a concentration of 400 ppma (parts per million actives).

The data in Table IV illustrates the significant reduction in intake valve deposits provided by the poly(oxyalkylene) hydroxyaromatic esters of the present invention (Example 3) compared to the base fuel. Moreover, the data in Table IV further demonstrates the significant reduction in combustion chamber deposits produced by the poly(oxyalkylene) hydroxyaromatic ethers of the present invention (Example 3) compared to a known polyisobutylphenol fuel additive (Comparative Example A).

What is claimed is:

1. A compound of the formula:

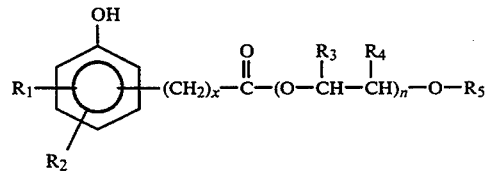

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms;

$R_3$ and $R_4$ are each hydrogen or ethyl, wherein one of $R_3$ and $R_4$ is ethyl and the other is hydrogen;

$R_5$ is hydrogen, phenyl, aralkyl or alkaryl having 7 to 36 carbon atoms, or an acyl group having the formula:

wherein $R_6$ is alkyl having 1 to 30 carbon atoms, phenyl, or aralkyl or alkaryl having 7 to 36 carbon atoms;

n is an integer from 5 to 100; and x is an integer from 0 to 10.

2. The compound according to claim 1, wherein n is an integer ranging from 10 to 50.

3. The compound according to claim 2, wherein n is an integer ranging from 15 to 30.

4. The compound according to claim 2, wherein $R_1$ is hydrogen, hydroxy, or lower alkyl having 1 to 4 carbon atoms; and $R_2$ is hydrogen.

5. The compound according to claim 4, wherein $R_5$ is hydrogen, or alkylphenyl having an alkyl group containing 4 to 24 carbon atoms.

6. The compound according to claim 5, wherein $R_1$ is hydrogen or hydroxy.

7. The compound according to claim 6, wherein $R_5$ is hydrogen, or alkylphenyl having an alkyl group containing 4 to 12 carbon atoms.

8. The compound according to claim 7, wherein x is 0, 1 or 2.

9. The compound according to claim 8, wherein $R_1$ is hydrogen, $R_5$ is alkylphenyl having an alkyl group containing 4 to 12 carbon atoms, and x is 0.

10. A fuel composition comprising a major amount of hydrocarbons boiling in the gasoline or diesel range and an effective detergent amount of a compound of the formula:

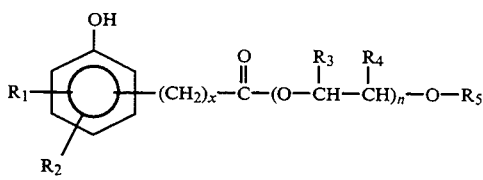

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group of the formula:

wherein $R_6$ is alkyl having 1 to 30 carbon atoms, phenyl, or aralkyl or alkaryl having 7 to 36 carbon atoms;

n is an integer from 5 to 100; and x is an integer from 0 to 10.

11. The fuel composition according to claim 10, wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30 and x is 0, 1 or 2.

12. The fuel composition according to claim 11 wherein $R_1$ is hydrogen or hydroxy; $R_5$ is hydrogen, alkyl having 4 to 12 carbon atoms, or alkylphenyl having an alkyl group containing 4 to 12 carbon atoms; and x is 0.

13. The fuel composition according to claim 12, wherein $R_1$ is hydrogen, and $R_5$ is alkylphenyl having an alkyl group containing 4 to 12 carbon atoms.

14. The fuel composition according to claim 10, wherein said composition contains about 50 to about 2500 parts per million by weight of said compound.

15. A fuel concentrate comprising an inert stable oleophilic organic solvent boiling in the range of from about 150° F. to 400° F. and from about 10 to about 70 weight percent of a compound of the formula:

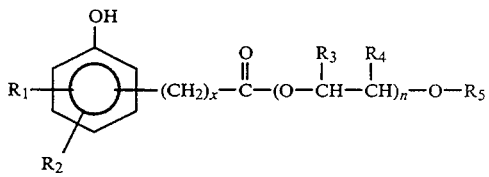

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group of the formula:

wherein $R_6$ is alkyl having 1 to 30 carbon atoms, phenyl, or aralkyl or alkaryl having 7 to 36 carbon atoms;

n is an integer from 5 to 100; and x is an integer from 0 to 10.

16. The fuel concentrate according to claim 15, wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to 22 carbon atoms, or alkylphenyl having an alkyl group containing 4 to 24 carbon atoms; n is 15 to 30 and x is 0, 1 or 2.

17. The fuel concentrate according to claim 16; wherein $R_1$ is hydrogen or hydroxy; $R_5$ is hydrogen, alkyl having 4 to 12 carbon atoms, or alkylphenyl having an alkyl group containing 4 to 12 carbon atoms; and x is 0.

18. The fuel concentrate according to claim 17, wherein $R_1$ is hydrogen, and $R_5$ is alkylphenyl having an alkyl group containing 4 to 12 carbon atoms.

* * * * *